United States Patent [19]
Puttner et al.

[11] Patent Number: 5,919,732
[45] Date of Patent: Jul. 6, 1999

[54] HERBICIDAL 3-ARYLAMINO-6-TRIFLUOROMETHYLURACILS

[75] Inventors: Reinhold Puttner; Jürgen Bohner; Hansjörg Krähmer, all of Berlin, Germany

[73] Assignee: Hoechst Schering AgrEvo GmbH, Berlin, Germany

[21] Appl. No.: 09/020,659

[22] Filed: Feb. 9, 1998

[30] Foreign Application Priority Data

Feb. 11, 1997 [DE] Germany .................. 197 05 012

[51] Int. Cl.$^6$ .................. A01N 43/48; C07D 239/02
[52] U.S. Cl. .................. 504/243; 544/311; 544/310; 544/309
[58] Field of Search .................. 544/309, 310, 544/311; 504/243

[56] References Cited

U.S. PATENT DOCUMENTS

| | | | |
|---|---|---|---|
| 3,580,913 | 5/1971 | Lutz | 260/260 |
| 4,411,839 | 10/1983 | Lindahl et al. | 260/465 D |
| 4,448,961 | 5/1984 | Lindahl, III et al. | 544/311 |
| 5,116,404 | 5/1992 | Ishii et al. | 71/92 |
| 5,593,945 | 1/1997 | Andree et al. | 504/243 |
| 5,681,794 | 10/1997 | Andree et al. | 504/243 |

FOREIGN PATENT DOCUMENTS

WO 95/04461  2/1995  WIPO .................. A01N 43/48

*Primary Examiner*—S. Mark Clardy
*Assistant Examiner*—Sabiha N. Qazi
*Attorney, Agent, or Firm*—Frommer Lawrence & Haug LLP

[57] ABSTRACT

There are described novel substituted 3-arylamino-6-trifluoromethyluracils of the formula I, processes for their preparation, and methods of controlling monocotyledonous and dicotyledonous harmful plants in agricultural and silvicultural crops.

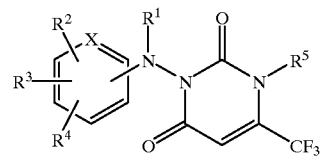

(I)

In formula I, the radicals $R^1$, $R^2$, $R^3$ and $R^4$ are not only hydrogen, alkyl and haloalkyl, but can also have further meanings, $R^5$ is alkyl or amino, and X is CH or N.

10 Claims, No Drawings

HERBICIDAL 3-ARYLAMINO-6-TRIFLUOROMETHYLURACILS

DESCRIPTION

Herbicidal 3-arylamino-6-trifluoromethyluracils

The invention relates to novel substituted 3-arylamino-6-trifluoromethyluracils, to their preparation, and to methods of controlling monocotyledonous and dicotyledonous harmful plants in agricultural and silvicultural crops.

Uracils having herbicidal properties and their use in the control of undesirable plant growth have been disclosed in a variety of publications.

U.S. Pat. No. 4,448,961 discloses uracils, which have an arylamino radical attached to them in the 1 position, as both fungicidally and herbicidally active compounds.

U.S. Pat. No. 3,580,913 and WO 95/04461 describe 3-benzyl-6-trifluoromethyluracils having herbicidal properties, the former document disclosing uracils which are unsubstituted in the 1 position, while the second document discloses 1-methyl-substituted uracils.

However, the desired herbicidal activity of the known compounds is frequently insufficient, or else a suitably high herbicidal activity may result in undesirable damage to the agricultural or silvicultural crops.

It is an object of the present invention to provide novel substituted 3-arylamino-6-trifluoromethyluracils which do not have these disadvantages and whose biological properties are superior to the compounds known to date.

It has now been found that substituted 3-arylamino-6-trifluoromethyluracils of the formula I

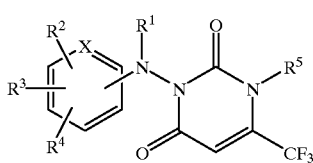

(I)

in which $R^1$ is hydrogen, $C_1$–$C_4$-alkyl, halo-$C_1$–$C_4$-alkyl, $C_1$–$C_4$-alkoxy-$C_1$–$C_4$-alkyl, $C_1$–$C_4$-alkoxycarbonyl-$C_1$–$C_4$-alkyl, formyl, $SO_2R^6$, $C_1$–$C_{10}$-alkylcarbonyl or $C_1$–$C_{10}$-alkoxycarbonyl, it being possible for the two last-mentioned radicals to be optionally substituted by one or more identical or different halogen atoms, $R^2$ is hydrogen, halogen, nitro, amino, cyano, $C_1$–$C_4$-alkyl, halo-$C_1$–$C_4$-alkyl, $C_1$–$C_4$-alkoxy, halo-$C_1$–$C_4$-alkoxy, $C_2$–$C_4$-alkenyloxy, $C_3$–$C_4$-alkynyloxy, $C_1$–$C_4$-alkoxycarbonyl, $C_1$–$C_4$-alkoxycarbonyl-$C_1$–$C_4$-alkoxy, carboxyl, aminocarbonyl, $C_1$–$C_4$-alkylaminocarbonyl, di-$C_1$–$C_4$-alkylaminocarbonyl or $C_1$–$C_4$-alkyl-sulfonyl, $R^3$ and $R^4$ independently of each other are hydrogen, halogen, nitro, cyano, $C_1$–$C_4$-alkyl, halo-$C_1$–$C_4$-alkyl, $C_1$–$C_4$-alkoxy or halo-$C_1$–$C_4$alkoxy, $R^5$ is $C_1$–$C_4$-alkyl or amino, $R^6$ is $C_1$–$C_6$-alkyl or $C_2$–$C_6$-alkenyl which is optionally substituted by one or more identical or different halogen atoms and X is CH or N, have a better herbicidal activity and a better crop plant tolerance in comparison with the known compounds.

Substituted 3-arylamino-6-trifluoromethyluracils of the formula I which have proved especially effective are those where $R^1$ is hydrogen, $C_1$–$C_3$-alkyl, $C_1$–$C_3$-alkyl which is mono- or polysubstituted by fluorine, chlorine or bromine, $C_1$–$C_4$-alkoxy-$C_1$–$C_2$-alkyl, $C_1$–$C_4$-alkoxycarbonyl-$C_1$–$C_2$-alkyl, formyl, $SO_2R^6$, $C_1$–$C_6$-alkyl-carbonyl or $C_1$–$C_6$-alkoxy-carbonyl, it being possible for the two last-mentioned radicals to be optionally substituted by one or more identical or different halogen atoms, $R^2$ is hydrogen, halogen, nitro, amino, cyano, $C_1$–$C_3$-alkyl, $C_1$–$C_3$-alkyl which is mono- or polysubstituted by fluorine, chlorine or bromine, methoxy, ethoxy, propoxy, isopropoxy, $C_1$–$C_3$-alkoxy which is mono- or polysubstituted by fluorine, chlorine or bromine, $C_2$–$C_4$-alkenyloxy, $C_3$–$C_4$-alkynyloxy, $C_1$–$C_3$-alkoxycarbonyl, $C_1$–$C_4$-alkoxycarbonyl-$C_1$–$C_2$-alkoxy, carboxyl, aminocarbonyl, $C_1$–$C_3$-alkylaminocarbonyl, di-$C_1$–$C_3$-alkylaminocarbonyl or $C_1$–$C_2$-alkylsulfonyl, $R^3$ and $R^4$ independently of one another are hydrogen, halogen, nitro, cyano, methyl, ethyl, trifluoromethyl, methoxy, ethoxy, propoxy, isopropoxy, $C_1$–$C_3$-alkoxy which is mono- or polysubstituted by fluorine, chlorine or bromine, $R^5$ is methyl, ethyl or amino, $R^6$ is $C_1$–$C_4$-alkyl or $C_2$–$C_4$-alkenyl which is optionally substituted by one or more identical or different halogen atoms, and X is CH or N.

Substituted 3-arylamino-6-trifluoromethyluracils of the formula I which have proved very especially effective are those where $R^1$ is hydrogen, $C_1$–$C_3$alkyl, $C_1$–$C_3$-alkyl which is mono- or polysubstituted by fluorine or chlorine, formyl, $SO_2R^6$, $C_1$–$C_4$-alkyl-carbonyl or $C_1$–$C_4$-alkoxycarbonyl, the two last-mentioned radicals optionally being substituted by one or more identical or different halogen atoms, $R^2$ is hydrogen, halogen, nitro, amino, cyano, $C_1$–$C_2$-alkyl, $C_1$–$C_2$-alkyl which is mono- or polysubstituted by fluorine or chlorine, methoxy, ethoxy, propoxy, isopropoxy, $C_1$–$C_2$-alkoxy which is mono- or polysubstituted by fluorine or chlorine, $C_2$–$C_3$-alkenyloxy, $C_3$–$C_4$-alkynyloxy, $C_1$–$C_3$-alkoxy-carbonyl, $C_1$–$C_2$-alkoxycarbonyl-$C_1$–$C_2$-alkoxy, carboxyl, aminocarbonyl, $C_1$–$C_2$-alkylaminocarbonyl, di-$C_1$–$C_2$-alkyl-aminocarbonyl or $C_1$–$C_2$-alkylsulfonyl, $R^3$ and $R^4$ independently of one another are hydrogen, halogen, methyl, ethyl, trifluoromethyl, methoxy, ethoxy, propoxy, isopropoxy, methoxy which is mono- or polysubstituted by fluorine or chlorine, $R^5$ is methyl, ethyl or amino, $R^6$ is $C_1$–$C_4$-alkyl or $C_2$–$C_4$-alkenyl which is optionally mono- or polysubstituted by identical or different halogen atoms from the group consisting of chlorine and fluorine, and X is CH or N.

The term "halogen" encompasses fluorine, chlorine, bromine and iodine.

The terms 'alkyl', 'alkenyl' and 'alkynyl' mean that the carbon chain can be branched or unbranched. The two last-mentioned terms are to be understood in such a way that the multiple bond can be in any position of the unsaturated radical in question.

The terms 'halo-$C_1$–$C_4$-alkyl' and 'halo-$C_1$–$C_4$-alkoxy' are to be understood as meaning that one or more hydrogen atoms of the hydrocarbon radical are replaced by identical or different halogen.

The terms di-$C_1$–$C_4$-alkylaminocarbonyl, di-$C_1$–$C_3$-alkylaminocarbonyl and di-$C_1$–$C_2$-alkylaminocarbonyl mean that the two alkyl radicals located on the nitrogen can be identical or different.

In formula I, and in the subsequent formulae II, III and IV, the radicals $R^2$, $R^3$ and $R^4$ and the uracilylamino radical can be positioned on any carbon atom of the benzene or pyridine ring.

The present invention also relates to the 3-arylamino-6-trifluoromethyluracils of the formula II

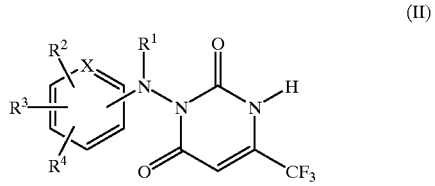

(II)

in which $R^1$, $R^2$, $R^3$, $R^4$ and X have the meanings given under formula I.

These compounds of the formula II are suitable as intermediates for the preparation of the compounds of the formula I.

In the event that $R^5$ is $C_1$–$C_4$-alkyl, the compounds of the formula I according to the invention can be prepared by reacting a compound of the formula II with an alkylating reagent in an inert solvent in the presence of a base at a suitable temperature.

In the event that $R^5$ is amino, the compounds of the formula I according to the invention can be prepared, for example, by reacting a compound of the formula II with a nitrozation reagent and subsequently reducing the resulting N-nitrosamine, or by base-catalyzed reaction with 2,4-dinitrophenoxyamine.

Depending on the nitrosation reagent used, the nitrosation reaction can be carried out at a suitable temperature in water, dilute hydrochloric acid, dilute sulfuric acid, glacial acetic acid or in an inert solvent.

The reduction is carried out in an inert solvent at a suitable temperature.

The reaction with 2,4-dinitrophenoxyamine is carried out in inert solvents, for example in dimethylformamide using bases such as, for example, sodium hydride, sodium carbonate or potassium carbonate.

Substances which are suitable as alkylation reagents for the preparation of the compounds of the formula I according to the invention are the corresponding alkyl halides, in particular the alkyl bromides and alkyl iodides, and also dialkyl sulfates.

Substances which are suitable from amongst the group of the inert solvents are aliphatic, cycloaliphatic and aromatic hydrocarbons, each of which can optionally be chlorinated, for example hexane, ligroin, petroleum ether, cyclohexane, benzene, toluene, xylene, methylene chloride, chloroform, carbon tetrachloride, ethylene chloride, trichloroethylene and chlorobenzene, ethers, for example diethyl ether, methyl ethyl ether, methyl-t-butyl ether, diisopropyl ether, dibutyl ether, 1,4-dioxane and tetrahydrofuran, ketones, for example acetone, methyl ethyl ketone, methyl isopropyl ketone and methyl isobutyl ketone, nitriles, for example acetonitrile and propionitrile, carboxylic esters, for example ethyl acetate and amyl acetate, carboxamides, for example dimethylformamide and dimethylacetamide, sulfoxides, for example dimethylsulfoxide, and sulfones, for example sulfolane.

Suitable bases are organic and inorganic bases, for example potassium carbonate, sodium carbonate, sodium hydride, potassium hydroxide, sodium hydroxide, sodium ethoxide, sodium methoxide, potassium t-butoxide, triethylamine, dimethylaminopyridine and pyridine.

The nitrosation can be carried out with customary nitrosation reagents such as alkali metal nitrites, nitrous acid or alkyl nitrites, for example t-butyl nitrite and amyl nitrite.

The subsequent reduction of the N-nitrosamines to give the compounds of the formula I according to the invention in which $R^5$ is amino can be carried out with complex hydrides, for example lithium aluminum hydride, lithium alkoxyaluminum hydride, lithium borohydride, sodium borohydride and sodium alkoxyborohydride.

The reaction temperature is expediently selected as a function of the boiling point of the solvent and as a function of the reactivity of the reactors and is in a range from −20 to 150° C., preferably between 0 and 70° C.

The resulting compounds according to the invention can be isolated from the reaction mixture by customary methods, for example by distilling off the solvent employed under atmospheric or reduced pressure, by precipitation with a suitable diluent or by extraction.

If purification should be necessary, this can be effected by customary methods, for example by crystallization or by chromatographic purification processes.

The intermediates of the formula II can be prepared by reacting, in an absolute solvent, ethyl 3-amino-4,4,4-trifluoromethylcrotonate, first of all with one of the above-mentioned bases and subsequently with a phenyl carbazate of the formula III,

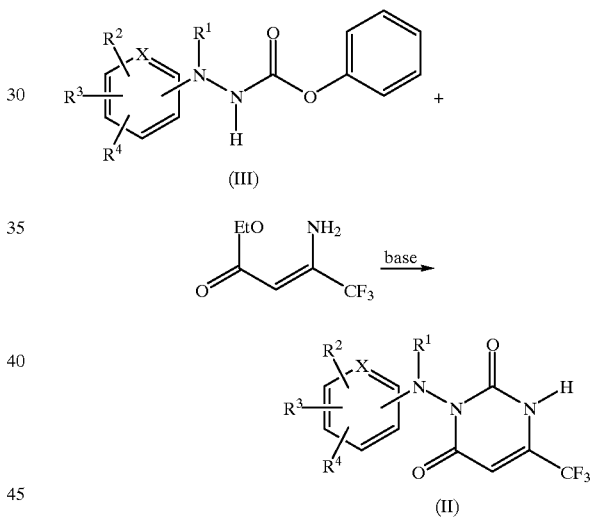

in which $R^1$, $R^2$, $R^3$, $R^4$ and X have the meanings given in the formula I.

For example, the reaction is carried out in such a manner that ethyl 3-amino-4,4,4-trifluoromethylcrotonate is introduced into absolute dimethylformamide at 0 to 5° C., with sodium hydride as the base. After adding a phenyl carbazate of the formula III, the mixture is heated to 100 to 130° C. The reaction mixture is hydrolyzed, acidified and extracted with an organic solvent.

Separating the intermediates of the formula II from the phenol formed during the reaction by treatment with soda solution and reliberating it by acidification has proved advantageous.

Further purification can be effected by crystallization or chromatographic purification methods.

The compounds of the formula III are either known or can be prepared by known processes from the correspondingly substituted arylhydrazines of the formula IV

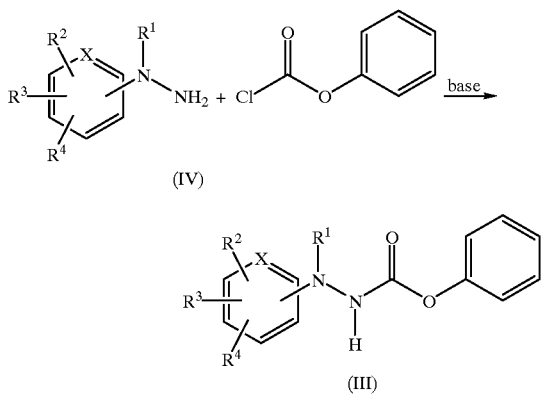

(IV)

(III)

in which $R^1$, $R^2$, $R^3$, and $R^4$ and X have the meanings given under the formula I, using phenyl chloroformate in the presence of one of the abovementioned bases.

The compounds of the formula IV are commercially available or can be prepared by known processes.

The compounds of the formula I according to the invention, also termed "active ingredients according to the invention" hereinbelow, have a good herbicidal activity against broad-leaved weeds and also against grasses. Due to their good crop plant tolerance, they may also be employed in a variety of agricultural crops, for example in oilseed rape, sugar beet, soybeans, cotton, rice, maize, barley, wheat and other cereal species. Individual compounds are especially suitable for use as selective herbicides in sugar beet, soybeans, cotton, maize and cereals. Equally, the compounds can be used for controlling undesirable harmful plants in perennial crops, for example afforestations, stands of ornamental trees, orchards, vineyards, citrus orchards, coffee plantations, tea plantations, rubber plantations, oil palm plantations, cocoa plantations, soft fruit fields and hop fields.

The active ingredients according to the invention can be used for example for controlling the following genera of plants:

dicotyledonous plants from the genera: Abutilon, Amaranthus, Ambrosia, Anthemis, Brassica, Centaurea, Chenopodium, Chrysanthemum, Cirsium, Convolvulus, Datura, Galeopsis, Galinsoga, Galium, Ipomoea, Lamium, Lepidium, Matricaria, Papaver, Pharbitis, Polygonum, Portulaca, Senecio, Sinapis, Sesbania, Solanum, Sonchus, Stellaria, Urtica, Veronica, Viola and Xanthium.

Monocotyledonous plants from the genera: Alopecurus, Apera, Avena, Brachiaria, Bromus, Cyperus, Digitaria, Echinochloa, Eleocharis, Eleusine, Elymus, Fimbristylis, Ischaemum, Lolium, Monochoria, Panicum, Poa, Sagittaria, Setaria and Sorghum.

The active ingredients according to the invention can be employed at a rate of application of between 0.001 and 5 kg/ha, both pre- and post-emergence.

In addition, they are also used as defoliants, desiccants and haulm killers.

The active ingredients according to the invention can be applied either alone, as a mixture with each other or in combination with other active ingredients. If appropriate, other crop protection products or pesticides may be added, depending on the intended aim. If it is desired to widen the spectrum of action, other herbicidally active ingredients may also be added. Active ingredients which are suitable for this purpose are, for example, those described in 'Weed Abstracts, Vol. 48, No. 2, 1994' under the title "List of common names and abbreviations employed for currently used herbicides and plant growth regulators".

Intensity and rate of action can be promoted for example by adding organic solvents, wetters and oils. Such additions may therefore permit a reduction in the dosage of the active ingredient.

The active ingredients according to the invention or their mixtures are expediently applied in the form of preparations such as powders, materials for spreading, granules, solutions, emulsions or suspensions, with the addition of liquid and/or solid carriers or diluents and, if appropriate, surfactants such as tackifying, wetting, emulsifying and/or dispersing auxiliaries.

Examples of suitable liquid carriers are aliphatic and aromatic hydrocarbons such as cyclohexane, toluene and xylene, ketones such as cyclohexanone and isophorone, other solvents such as dimethylformamide and dimethyl sulfoxide, and furthermore mineral oil fractions and vegetable oils.

Solid carriers which are suitable are minerals, for example attapulgite, bentonite, limestone, kaolin, silica gel and talc, and products of vegetable origin, for example meals.

Examples of surfactants to be mentioned are substituted benzenesulfonic acids and their salts, calcium lignosulfonate, fatty alcohol sulfates, formaldehyde condensates, naphthalenesulfonic acids and their salts, phenolsulfonic acids and their salts, and polyethylene alkylphenyl ethers.

The amount of active ingredient, or active ingredients, in the various products can vary within wide limits. For example, the herbicidally active compositions comprise approximately 10 to 90 percent by weight of active ingredient, approximately 90 to 10 percent by weight of liquid or solid carriers and, if appropriate, up to 20 percent by weight of surfactants.

The herbicidally active compositions can be applied in the customary manner, for example using water as the carrier, the rates of spray mixture amounting to approximately 100 to 1000 l/ha. Application of the compositions by the so-called low-volume and ultra-low-volume methods is equally possible, as is the application in the form of so-called microgranules.

The products can be prepared in a manner known per se, for example by grinding or mixing processes. If desired, products of the individual components may also be mixed only just prior to their use, as is carried out, for example, under practice conditions when using the so-called tank mix method.

To prepare the various products, for example the following components are employed:

A) wettable powder
  20 percent by weight of active ingredient
  35 percent by weight of attapulgite
  8 percent by weight of calcium lignosulfonate
  2 percent by weight of sodium N-methyl-N-oleyltaurinate
  35 percent by weight of silica gel B) emulsion concentrate
  20 percent by weight of active ingredient
  75 percent by weight of isophorone
  5 percent by weight of a mixture based on calcium lignosulfonate and sodium N-methyl-N-oleyltaurinate The examples which follow illustrate the preparation of the compounds according to the invention in greater detail.

EXAMPLE 1

3-(2,3-Dichloroanilino)-1-methyl-6-trifluoromethyluracil 52.5 g (0.154 mol) of 3-(2,3-dichloroanilino)-6-trifluoromethyluracil and 42.67 g (0.309 mol) of potassium carbonate are introduced into 700 ml of acetone. 27.74 g (0.22 mol) of dimethyl sulfate are added, with stirring, at room temperature. The mixture is subsequently refluxed for one hour. After cooling, the solids are filtered off with suction, and the filtrate is concentrated in vacuo. The pale brown crystalline residue is stirred with 500 ml of diisopropyl ether and filtered off with suction. This gives 49.5 g (91% of theory) of 3-(2,3-dichloroanilino)-1-methyl-6-trifluoromethyluracil with a melting point of 179° C. and a retention value of 0.49 (silica gel, hexane/ethyl acetate 1:1).

EXAMPLE 1a 3-(2,3-Dichloroanilino)-6-trifluoromethyluracil 7.5 g (0.25 mol) of sodium hydride (80% dispersion in mineral oil) are introduced into 200 ml of absolute dimethylformamide. 45.7 g (0.25 mol) of ethyl 3-amino-4,4,4-trifluoromethylcrotonate, dissolved in 100 ml of absolute dimethylformamide, are added dropwise in the course of 15 minutes at 0 to 5° C., with stirring and cooling, and stirring is continued for a further 30 minutes without cooling. 63 g (0.212 mol) of phenyl 3-(2,3-dichlorophenyl)carbazate, dissolved in 500 ml of absolute dimethylformamide, are subsequently added dropwise in the course of 10 minutes. Thereupon, the mixture is stirred for 3 hours at 130° C. After the reaction mixture has been left to stand overnight, it is substantially concentrated in vacuo, the residue is taken up in 2 l of water, and the mixture is washed twice using in each case 1 l of diethyl ether. The aqueous phase is brought to pH 4 to 5 using 20 ml of concentrated hydrochloric acid and extracted twice using in each case 1 l of diethyl ether. The combined diethyl ether extracts are extracted twice using in each case 250 ml of soda solution. The combined soda extracts are washed with 1 l of diethyl ether, brought to pH 4 to 5 using 70 ml of concentrated hydrochloric acid, and extracted twice using in each case 1 l of diethyl ether. The combined diethyl ether phases are dried with magnesium sulfate, filtered and evaporated fully in vacuo. The pale brown crystalline residue is stirred with 1 l of a 1:1 mixture of diisopropyl ether and hexane. After the solid has been filtered off with suction and dried, 52.9 g (73.3% of theory) of 3-(2,3-dichloroanilino)-6-trifluoro-methyluracil with a melting point of 250° C. are obtained.

The compounds of the formula I according to the invention which are listed in Table 1 can be prepared analogously to Example I:

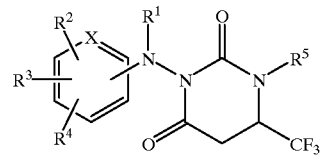

(I)

TABLE 1

| Ex. No. | X | $R^1$ | $R^2$ | $R^3$ | $R^4$ | $R^5$ | M.p. [° C.] |
|---|---|---|---|---|---|---|---|
| 2 | CH | $CH_3$ | 2-Cl | 3-Cl | H | $CH_3$ | 175.5 |
| 3 | CH | H | 2-Cl | 3-Cl | 5-Cl | $NH_2$ | |
| 4 | CH | H | 2-Cl | 3-Cl | 5-I | $CH_3$ | |
| 5 | CH | $CH_3$ | 2-Cl | 3-Cl | 5-$OCF_2H$ | $CH_3$ | |
| 6 | CH | H | 2-Cl | 3-O-i-$C_3H_7$ | 4-Cl | $CH_3$ | |
| 7 | CH | H | 2-Cl | 3-$OCH_3$ | 4-Cl | $CH_3$ | |
| 8 | CH | H | 2-Cl | 3-I | H | $CH_3$ | |
| 9 | CH | H | 2-Cl | H | H | $CH_3$ | 159 |
| 10 | CH | H | 2-Cl | 3-Cl | 4-I | $CH_3$ | |
| 11 | CH | H | 2-Cl | 3-$OCF_3$ | H | $CH_3$ | |
| 12 | CH | H | 2-Cl | 5-Cl | H | $CH_3$ | 218 |
| 13 | CH | H | 2-Cl | 4-Cl | 5-Cl | $CH_3$ | 192.5 |
| 14 | CH | H | 2-Cl | 4-Cl | H | $CH_3$ | 124 |
| 15 | CH | H | 2-Cl | 3-Cl | 4-Cl | $CH_3$ | 183 |
| 16 | CH | H | 3-Cl | 4-Cl | 5-Cl | $CH_3$ | |
| 17 | 2-N | H | 3-Cl | H | H | $CH_3$ | |
| 18 | CH | H | 3-Cl | 4-Cl | H | $CH_3$ | 143 |
| 19 | 3-N | H | 3-Cl | 4-Cl | H | $CH_3$ | |
| 20 | CH | H | 3-Cl | 5-Cl | H | $CH_3$ | 148 |
| 21 | CH | H | 3-Cl | H | H | $CH_3$ | 115 |
| 22 | CH | H | 4-Cl | H | H | $CH_3$ | 137 |
| 23 | CH | H | 3-Br | H | 5-F | $CH_3$ | |
| 24 | CH | H | 3-Br | 4-$OCF_2H$ | H | $NH_2$ | |
| 25 | CH | H | 3-Br | H | H | $CH_3$ | 161 |
| 26 | CH | $CO_2C_2H_5$ | 2-I | H | 5-F | $CH_3$ | |
| 27 | CH | H | 3-I | H | 5-I | $CH_3$ | |
| 28 | 3-N | $CH_3$ | 4-I | H | 5-Cl | $CH_3$ | |
| 29 | CH | H | 2-F | H | H | $CH_3$ | 138 |
| 30 | CH | H | 3-F | H | H | $CH_3$ | 127 |
| 31 | CH | H | 2-CN | 3-$CH_3$ | 4-$CF_3$ | $CH_3$ | |
| 32 | 3-N | H | 2-CN | H | H | $CH_3$ | |
| 33 | 3-N | $CH_3$ | 2-CN | H | H | $CH_3$ | |
| 34 | 2-N | H | 4-CN | H | H | $CH_3$ | |
| 35 | CH | H | 2-$NO_2$ | 4-Cl | H | $CH_3$ | |
| 36 | CH | $C_2H_5$ | 2-$NO_2$ | H | H | $CH_3$ | |
| 37 | CH | $(CH_2)_2CO_2CH_3$ | 2-$CH_3$ | 3-I | H | $CH_3$ | |
| 38 | CH | H | 2-$C_2H_5$ | 3-Cl | 5-Cl | $CH_3$ | |
| 39 | CH | $COCH_3$ | 2-i-$C_3H_7$ | 3-F | H | $CH_3$ | |
| 40 | CH | H | 2-$CF_3$ | H | H | $CH_3$ | 137 |
| 41 | CH | CHO | 2-$CF_3$ | 3-$OCH_3$ | H | $CH_3$ | |

TABLE 1-continued

| Ex. No. | X | R¹ | R² | R³ | R⁴ | R⁵ | M.p. [° C.] |
|---|---|---|---|---|---|---|---|
| 42 | CH | $CH_3$ | 2-$OCF_2H$ | H | H | $NH_2$ | |
| 43 | 4-N | H | 3-$OCF_2H$ | H | H | $CH_3$ | |
| 44 | 4-N | H | 2-$OCH_3$ | H | H | $CH_3$ | |
| 45 | CH | H | 2-O-i-$C_3H_7$ | H | 5-Br | $NH_2$ | |
| 46 | CH | H | 2-$OCH_2CH=CH_2$ | 3-F | H | $CH_3$ | |
| 47 | CH | $CH_3$ | 2-$OCH_2C\equiv CH$ | 3-Cl | 4-Cl | $CH_3$ | |
| 48 | CH | H | 5-O-CH=$CH_3$ | 4-Cl | 3-Cl | $CH_3$ | |
| 49 | CH | H | 2-$O(CH_2)_2CO_2CH_3$ | H | 4-F | $CH_3$ | |
| 50 | CH | H | 5-$CONHC_2H_5$ | 3-Cl | H | $CH_3$ | |
| 51 | 4-N | $CH_3$ | 2-CO-$N(CH_3)_2$ | H | H | $CH_3$ | |
| 52 | 3-N | H | 2-$CONH_2$ | H | H | $CH_3$ | |
| 53 | CH | $COCH_3$ | 3-CONH | 5-Cl | H | $CH_3$ | |
| 54 | CH | $(CH_2)_2OCH_3$ | 3-COOH | 4-Br | 5-Cl | $CH_3$ | |
| 55 | 2-N | H | 4-COOH | H | H | $CH_3$ | |
| 56 | CH | H | 5-$CO_2C_2H_5$ | 3-Cl | H | $CH_3$ | |
| 57 | 2-N | H | 4-CONH-i-$C_3H_7$ | H | H | $CH_3$ | |
| 58 | CH | $COOCH_3$ | 4-$SO_2CH_3$ | 3-Cl | H | $CH_3$ | |
| 59 | CH | H | 2-Cl | 4-Cl | 6-Cl | $CH_3$ | 116–120 |
| 60 | CH | H | 2-Cl | H | 6-Cl | $CH_3$ | 125 |
| 61 | CH | H | 2-F | H | 5-F | $CH_3$ | 147–152 |
| 62 | CH | H | H | 4-$CF_3$ | H | $CH_3$ | 90 |
| 63 | CH | H | 2-$CH_3$ | 4-Cl | H | $CH_3$ | 144–148 |
| 64 | CH | H | 3-Cl | 4-$CH_3$ | H | $CH_3$ | 114–118 |
| 65 | CH | H | 2-F | 4-F | H | $CH_3$ | 110 |
| 66 | CH | H | 4-$CH_3$ | H | H | $CH_3$ | 89 |
| 67 | CH | H | 2-$CH_3$ | H | H | $CH_3$ | 127 |
| 68 | CH | H | 2-$CH_3$ | 5-$CH_3$ | H | $CH_3$ | 133–136 |
| 69 | CH | H | 2-$CH_3$ | 3-$CH_3$ | H | $CH_3$ | 151–155 |
| 70 | CH | H | 2-Cl | 5-$CF_3$ | H | $CH_3$ | 165 |
| 71 | CH | H | 3-$OCH_3$ | 5-$OCH_3$ | H | $CH_3$ | 93 |
| 72 | CH | H | 2-F | 3-Cl | 4-F | $CH_3$ | 148 |
| 73 | CH | H | 5-$CONHC_2H_5$ | 2-Cl | H | $CH_3$ | 92–106 |
| 74 | CH | H | 5-CONH-i-$C_3H_7$ | 2-Cl | H | $CH_3$ | 111–118 |
| 75 | CH | H | 5-CO—NH-t-$C_4H_9$ | 2-Cl | H | $CH_3$ | 174–177 |
| 76 | CH | H | 2-Cl | 3-CN | 4-Cl | $CH_3$ | 195–205 |
| 77 | CH | H | 2-F | 3-F | H | $CH_3$ | 101 |
| 78 | CH | H | 2-Br | 4-Br | H | $CH_3$ | 136 |
| 79 | CH | H | 2-Br | 3-F | H | $CH_3$ | 144 |
| 80 | CH | H | 2-CN | 3-F | H | $CH_3$ | 300 Mhz-¹H NMR ($CDCl_3$): δ = 7.40 ($m_c$, 1H, 5'-H), 7.18 (s, 1H, NH), 6.74 (dd, 1H, 4'-H, J = 7 Hz), 6.46 (d, 1H, 6'-H, J = 7 Hz), 6.38 (s, 1H, 5-H), 3.58 (s, 3H, N—$CH_3$). |
| 81 | CH | H | 2-CN | 3-Cl | H | $CH_3$ | 300 Mhz-¹H NMR ($CDCl_3$): δ = 7.35 (t, 1H, 5'-H J = 7 Hz), 7.07 (s, 1H, NH), 7.05 (d, 1H, 4'-H, J = 7 Hz), 6.54 (d, 1H, 6'-H, J = 7 Hz), 6.38 (s, 1H, 5-H), 3.58 (s, 3H, N—$CH_3$). |
| 82 | CH | H | 2-Br | 3-F | 4-Br | $CH_3$ | 90 |
| 83 | CH | H | 2-CN | 3-CN | H | $CH_3$ | |
| 84 | CH | H | 2-CN | 3-$OCH_3$ | H | $CH_3$ | |
| 85 | CH | H | 2-Br | 3-Br | H | $CH_3$ | |
| 86 | CH | H | 2-Br | 3-Br | 4-Br | $CH_3$ | |
| 87 | CH | H | 2-Br | 3-Cl | H | $CH_3$ | |
| 88 | CH | H | 2-Br | 3-Cl | 4-Br | $CH_3$ | |
| 89 | CH | H | 3-Br | 4-Br | H | $CH_3$ | |
| 90 | CH | H | 2-F | 3-F | 4-F | $CH_3$ | |
| 91 | CH | H | 4-F | H | H | $CH_3$ | 124 |
| 92 | CH | H | 4-F | H | H | $CH_3$ | 110 |
| 93 | CH | H | 2-$NO_2$ | 4-$NO_2$ | H | $CH_3$ | 199–203 |
| 94 | CH | H | 2-$NO_2$ | 4-$CF_3$ | H | $CH_3$ | 142–145 |
| 95 | CH | H | 2-$NO_2$ | 4-$CF_3$ | 6-$NO_2$ | $CH_3$ | 211 |
| 96 | CH | H | 2-Cl | 4-$NO_2$ | 6-Cl | $CH_3$ | 50–55 |
| 97 | CH | H | 2-Cl | 4-$NO_2$ | 5-$CF_3$ | $CH_3$ | 162–168 |
| 98 | CH | H | 2-Cl | 3-Cl | 4-Br | $CH_3$ | 174 |
| 99 | CH | H | 2-Cl | 3-Cl | 4-$NO_2$ | $CH_3$ | 188 |
| 100 | CH | H | 2-$NO_2$ | 4-$NO_2$ | H | $CH_3$ | 108 |
| 101 | CH | H | 4-$NO_2$ | H | H | $CH_3$ | 128–132 |
| 102 | CH | H | 2-Cl | 4-Cl | 6-Cl | $NH_2$ | 175 |
| 103 | CH | H | 2-Cl | 6-Cl | H | $NH_2$ | 153 |
| 104 | CH | H | 2-F | 4-F | H | $NH_2$ | 138 |
| 105 | CH | H | 2-F | 5-F | H | $NH_2$ | 155 |
| 106 | CH | H | 4-$CF_3$ | H | H | $NH_2$ | 68 |
| 107 | CH | H | 2-Cl | 5-$CF_3$ | H | $NH_2$ | 170 |
| 108 | CH | H | 2-F | 3-Cl | 4-F | $NH_2$ | 50 |
| 109 | CH | H | 3-$OCH_3$ | 5-$OCH_3$ | H | $NH_2$ | 181 |
| 110 | CH | H | 2-$CH_3$ | H | H | $NH_2$ | 160 |

TABLE 1-continued

| Ex. No. | X | R¹ | R² | R³ | R⁴ | R⁵ | M.p. [° C.] |
|---|---|---|---|---|---|---|---|
| 111 | CH | H | 4-CH₃ | H | H | NH₂ | 150 |
| 112 | CH | H | 2-CH₃ | 3-CH₃ | H | NH₂ | 212 |
| 113 | CH | H | 2-CH₃ | 5-CH₃ | H | NH₂ | 217–221 |
| 114 | CH | H | 2-CH₃ | 4-Cl | H | NH₂ | 198 |
| 115 | CH | H | 2-Cl | 3-CN | 4-Cl | NH₂ | 81–86 |
| 116 | CH | H | 5-CONHC₂H₅ | 2-Cl | H | NH₂ | 229 |
| 117 | CH | H | 5-CONH-i-C₃H₇ | 2-Cl | H | NH₂ | 96–102 |
| 118 | CH | H | 5-CONH-t-C₄H₉ | 2-Cl | H | NH₂ | 112 |
| 119 | CH | H | H | H | H | NH₂ | 155–159 |
| 120 | CH | H | 2-NO₂ | 4-NO₂ | H | NH₂ | 220 |
| 121 | CH | H | 3-Cl | 4-CH₃ | H | NH₂ | 200 Mhz-¹H NMR (D₆-DMSO): δ = 8.72 (s, 1H, NH), 7.12 (d, 1H, 5'-H, J = 8 Hz), 6.79 (d, 1H, 2'-H, J = 2 Hz), 6.61 (dd, 1H, 6'-H, J = 2 Hz, J = 8 Hz), 6.31 (s, 1H, 5-H), 5.52 (s, 2H, NH₂), 2.20 (s, 3H, CH₃). |
| 122 | CH | H | 2-F | 3-F | H | NH₂ | 127 |
| 123 | CH | H | 2-Br | 4-Br | H | NH₂ | 185 |
| 124 | CH | H | 2-Br | 3-F | H | NH₂ | |
| 125 | CH | H | 2-CN | 3-F | H | NH₂ | |
| 126 | CH | H | 2-CN | 3-Cl | H | NH₂ | |
| 127 | CH | H | 2-Br | 3-F | 4-Br | NH₂ | |
| 128 | CH | H | 2-CN | 3-CN | H | NH₂ | |
| 129 | CH | H | 2-CN | 3-OCH₃ | H | NH₂ | |
| 130 | CH | H | 2-Br | 3-Br | H | NH₂ | |
| 131 | CH | H | 2-Br | 3-Br | 4-Br | NH₂ | |
| 132 | CH | H | 2-Br | 3-Cl | H | NH₂ | |
| 133 | CH | H | 2-Br | 3-Cl | 4-Br | NH₂ | |
| 134 | CH | H | 3-Br | 4-Br | H | NH₂ | |
| 135 | CH | H | 2-F | 3-F | 4-F | NH₂ | — |
| 136 | CH | H | 4-F | H | H | NH₂ | — |
| 137 | CH | CH₃ | 2-Cl | 3-Cl | H | NH₂ | 160–163 |
| 138 | CH | CH₃ | 2-F | 5-F | H | NH₂ | 181 |
| 139 | CH | CH₃ | 2-F | 3-Cl | 4-F | CH₃ | 155 |
| 140 | CH | CH₃ | 2-Cl | 3-Cl | 4-Br | CH₃ | 168 |
| 141 | CH | CH₃ | 2-Cl | 3-Cl | 4-NO₂ | CH₃ | 188 |
| 142 | CH | CH₃ | 2-Br | 4-Br | H | CH₃ | 300 Mhz-¹H NMR (CDCl₃): δ = 7.61 (d, 1H, 3'-H, J = 1 Hz), 7.43 (dd, 1H, 5'-H, J = 7 Hz, J = 1 Hz), 7.18 (d, 1H, 6'-H, J = 7 Hz), 6.25 (s, 1H, 5-H), 3.48 (s, 3H, N—CH₃), 3.30 (s, 3H, N—CH₃). |
| 143 | CH | H | 2-Cl | 4-Cl | 6-Cl | C₂H₅ | 108 |
| 144 | CH | H | 2-Cl | 3-Cl | H | C₂H₅ | 138 |
| 145 | CH | H | 2-Cl | 3-Cl | H | i-C₃H₇ | 200 Mhz-¹H NMR (D₆-DMSO): δ = 8.63 (s, 1H, NH), 7.20–7.04 (m, 2H, 4'-H, 5'-H), 6.80 (s, 1H, 5-H), 6.58 (dd, 1H, 6'-H, J = 2 Hz, J = 8 Hz), 5.26 (sept., 1H, CH, J = 7 Hz), 1.24 (d, 6H, 2x CH₃, J = 7 Hz). |
| 146 | CH | H | 2-Cl | 3-Cl | H | n-C₃H₇ | 150 |
| 147 | CH | H | 2-Cl | 3-Cl | H | n-C₄H₉ | 95–100 |
| 148 | CH | COCH₃ | 4-CF₃ | H | H | CH₃ | 125 |
| 149 | CH | COCH₃ | 2-Cl | 3-Cl | H | CH₃ | 195 |
| 150 | CH | COC₂H₅ | 2-Cl | 3-Cl | H | CH₃ | 62 |
| 151 | CH | CO-i-C₃H₇ | 2-Cl | 3-Cl | H | CH₃ | 72–76 |
| 152 | CH | CO-cyclo-C₃H₅ | 2-Cl | 3-Cl | H | CH₃ | 90 |
| 153 | CH | COCH₃ | 2-CH₃ | 3-CH₃ | H | CH₃ | 300 Mhz-¹H (D₆-DMSO): δ = 7.44–7.02 (m, 3H, 4'-H, 5'-H, 6'-H), 6.61 (6.46)* (s, 1H, 5-H), 3.30 (s, 3H, N—CH₃), 2.42*–1.90* (6x s, 9H, 3x CH₃). *: double signal set due to E/Z-amide isomerism |
| 154 | CH | COCH₃ | 3-OCH₃ | 5-OCH₃ | H | CH₃ | 110–113 |
| 155 | CH | COCH₃ | 2-Cl | 6-Cl | H | CH₃ | 70 |
| 156 | CH | COCH₃ | 2-Cl | 4-Cl | 6-Cl | CH₃ | 67 |
| 157 | CH | COCH₃ | 2-F | 5-F | H | CH₃ | 158 |
| 158 | CH | COCH₃ | 2-F | 4-F | H | CH₃ | 51–54 |
| 159 | CH | COCH₃ | 2-F | 3-Cl | 4-F | CH₃ | 52 |
| 160 | CH | COCH₃ | 2-Cl | 5-CF₃ | H | CH₃ | 50 |
| 161 | CH | COCH₃ | 2-CH₃ | 4-Cl | H | CH₃ | 300 Mhz-¹H NMR (D₆-DMSO): δ = 7.6–7.0 (m, 3H, 3'-H, 5'-H, 6'-H), 6.61 (s, 1H, 5-H), 3.40 (s, 3H, N—CH₃), 2.38*–1.94* (4x s, 6H, 2x CH₃). *: double signal set due to E/Z-amide isomerism |
| 162 | CH | COCH₃ | 5-CONHC₂H₅ | 2-Cl | H | CH₃ | 200 Mhz-¹H NMR (D₆-DMSO): δ = 8.70–7.57 (m, 4H, NH, 3'-H, 4'-H, 6'-H), |

TABLE 1-continued

| Ex. No. | X | R¹ | R² | R³ | R⁴ | R⁵ | M.p. [° C.] |
|---|---|---|---|---|---|---|---|
| | | | | | | | 6.67 (s, 1H, 5-H), 4.02 (q, 2H, $CH_2$, J = 7 Hz), 3.40 (s, 3H, N—$CH_3$), 2.04 (1.99)* (s, 3H, $COCH_3$), 1.18 (t, 3H, $CH_3$, J = 7 Hz).<br>*: double signal set due to E/Z-amide isomerism |
| 163 | CH | $COCH_3$ | 5-CONH-i-$C_3H_7$ | 2-Cl | H | $CH_3$ | 200 Mhz-¹H NMR ($D_6$-DMSO): δ = 8.63–7.58 (m, 4H, NH, 3'-H, 4'-H, 6'-H), 6.68 (s, 1H, 5-H), 4.02 ($m_c$, 1H, CH), 3.32 (s, 3H, N—$CH_3$), 2.02 (s, 3H, $COCH_3$), 1.2–1.0 (m, 6H, 2x $CH_3$). |
| 164 | CH | $COCH_3$ | 5-CONH-t-$C_4H_9$ | 2-Cl | H | $CH_3$ | 200 Mhz-¹H NMR ($D_6$-DMSO): δ = 8.24–7.28 (m, 4H, NH, 3'-H, 4'-H, 6'-H), 6.70 (s, 1H, 5-H), 3.30 (s, 3H, N—$CH_3$), 2.05 (s, 3H, $COCH_3$), 1.38 (1.36)* (s, 9H, $C(CH_3)_3$).<br>*: double signal set due to E/Z-amide isomerism |
| 165 | CH | CO-i-$C_3H_7$ | 2-Br | 4-Br | H | $CH_3$ | 300 Mhz-¹H NMR ($CDCl_3$): δ = 7.87 (d, 1H, 3'-H, J = 0.5 Hz), 7.4–7.6 (br m, 2H, 5'-H, 6'-H), 6.30 (6.22)* (s, 1H, 5-H), 3.49 (3.53)* (s, 3H, N—$CH_3$), 2.65 (sept., 1H, COCH, J = 6 Hz), 1.13 (d, 3H, $CH_3$, J = 6 Hz), 1.07 (d, 3H, $CH_3$, J = 6 Hz).<br>*: double signal set due to E/Z-amide isomerism |
| 166 | CH | CO-cyclo-$C_3H_5$ | 2-Br | 4-Br | H | $CH_3$ | 300 Mhz-¹H NMR ($CDCl_3$): δ = 7.90 d, 1H, 3'-H, J = 0.5 Hz), 7.4–7.8 (br m, 2H, 5'-H, 6'-H), 6.32 (6.24) (s, 1H, 5-H), 3.50 (3.54) (s, 3H, N—$CH_3$), 09.–1.6 (br m, 5H, cyclopropyl-H).<br>*: double signal set due to E/Z-amide isomerism |
| 167 | CH | $COCF_3$ | 2-Cl | 3-Cl | H | $CH_3$ | 135 |
| 168 | CH | $COCClF_2$ | 2-Cl | 3-Cl | H | $CH_3$ | |
| 169 | CH | $COCCl_3$ | 2-Cl | 3-Cl | H | $CH_3$ | |
| 170 | CH | $COCBr_3$ | 2-Cl | 3-Cl | H | $CH_3$ | |
| 171 | CH | $COC_2F_5$ | 2-Cl | 3-Cl | H | $CH_3$ | |
| 172 | CH | CO-n-$C_3F_7$ | 2-Cl | 3-Cl | H | $CH_3$ | |
| 173 | CH | CO-n-$C_4F_9$ | 2-Cl | 3-Cl | H | $CH_3$ | |
| 174 | CH | $COCF_3$ | 2-Br | 4-Br | H | $CH_3$ | 49 |
| 175 | CH | $COCF_3$ | 2-Br | 3-F | H | $CH_3$ | |
| 176 | CH | $COCF_3$ | 2-Br | 3-F | 4-Br | $CH_3$ | |
| 177 | CH | $COCF_3$ | 2-Cl | 3-Cl | 4-Cl | $CH_3$ | |
| 178 | CH | $COCF_3$ | 2-Cl | 3-Cl | 4-Br | $CH_3$ | |
| 179 | CH | $COCF_3$ | 2-Cl | 3-Cl | 4-$NO_2$ | $CH_3$ | |
| 180 | CH | $COCF_3$ | 2-Cl | 3-CN | 4-Cl | $CH_3$ | |
| 181 | CH | $COCF_3$ | 2-F | 3-F | H | $CH_3$ | |
| 182 | CH | $COCF_3$ | 2-CN | 3-Cl | H | $CH_3$ | |
| 183 | CH | $SO_2CH_3$ | 2-Cl | 3-Cl | H | $CH_3$ | 121 |
| 184 | CH | $SO_2C_2H_5$ | 2-Cl | 3-Cl | H | $CH_3$ | 157 |
| 185 | CH | $SO_2CH_2Cl$ | 2-Cl | 3-Cl | H | $CH_3$ | 62–66 |
| 186 | CH | $SO_2CH=CH_2$ | 2-Cl | 3-Cl | H | $CH_3$ | 120 |
| 187 | CH | $SO_2CH_3$ | 2-Br | 4-Br | H | $CH_3$ | 300 Mhz-¹H NMR ($CDCl_3$): δ = 8.26 (d, 1H, 6'-H, J = 8 Hz), 7.83 (d, 1H, 3'-H, J = 1 Hz), 7.52 (dd, 1H, 5'-H, J = 1 Hz, J = 8 Hz), 6.26 (s, 1H, 5-H), 3.51 (s, 3H, N—$CH_3$), 3.40 (s, 3H, $SO_2$—$CH_3$). |
| 188 | 2-N | H | 4-$NO_2$ | H | H | $CH_3$ | 163–166 |
| 189 | 2-N | H | 4-$CF_3$ | H | H | $CH_3$ | 200 Mhz-¹H NMR ($CDCl_3$): δ = 8.42 (d, 1H, 6'-H, J = 1 Hz), 8.18 (s, 1H, NH), 7.70 (dd, 1H, 4'-H, J = 1 Hz, J = 8 Hz), 6.75 (d, 1H, 3'-H, J = 8 Hz), 6.40 (s, 1H, 5-H), 3.58 (s, 3H, N—$CH_3$). |
| 190 | 2-N | H | 3-F | H | H | $CH_3$ | 139–143 |
| 191 | 2-N | H | 3-Cl | H | H | $CH_3$ | 200 Mhz-¹H NMR ($CDCl_3$): δ = 7.50 (t, 1H, 4'-H, J = 7 Hz), 7.26 (s, 1H, NH), 6.90 (d, 1H, 5'-H, J = 7 Hz), 6.59 (d, 1H, 3'-H, J = 7 Hz), 6.39 (s, 1H, 5-H), 3.58 (s, 3H, N—$CH_3$). |
| 192 | 2-N | CO—$CF_3$ | 3-Cl | H | H | $CH_3$ | |
| 193 | 2-N | H | 3-Cl | H | H | $NH_2$ | |
| 194 | 3-N | H | 2-Cl | H | H | $CH_3$ | |
| 195 | 3-N | H | 2-Cl | 4-Cl | H | $CH_3$ | |
| 196 | 3-N | H | 4-Cl | H | H | $CH_3$ | |
| 197 | 3-N | H | 4-Cl | H | H | $NH_2$ | |
| 198 | 3-N | $COCF_3$ | 2-Cl | 4-Cl | H | $CH_3$ | |

TABLE 1-continued

| Ex. No. | X | $R^1$ | $R^2$ | $R^3$ | $R^4$ | $R^5$ | M.p. [° C.] |
|---|---|---|---|---|---|---|---|
| 199 | 4-N | H | 2-Cl | 3-Cl | H | $CH_3$ | |
| 200 | 4-N | H | 2-F | 3-F | H | $CH_3$ | |

The compounds of the formula II listed in Table 2 can be prepared analogously to Example 1a:

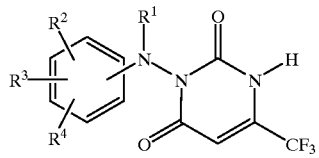
(II)

TABLE 2

| Ex. No. | X | $R^1$ | $R^2$ | $R^3$ | $R^4$ | M.p. [° C.] |
|---|---|---|---|---|---|---|
| 2a | CH | $CH_3$ | 2-Cl | 3-Cl | H | 203 |
| 3a | CH | H | 2-Cl | 3-Cl | 5-Cl | |
| 4a | CH | H | 2-Cl | 3-Cl | 5-I | |
| 5a | CH | $CH_3$ | 2-Cl | 3-Cl | 5-$OCF_2H$ | |
| 6a | CH | H | 2-Cl | 3-O-i-$C_3H_7$ | 4-Cl | |
| 7a | CH | H | 2-Cl | 3-$OCH_3$ | 4-Cl | |
| 8a | CH | H | 2-Cl | 3-I | H | |
| 9a | CH | H | 2-Cl | H | H | 217 |
| 10a | CH | H | 2-Cl | 3-Cl | 4-I | |
| 11a | CH | H | 2-Cl | 3-$OCF_3$ | H | |
| 12a | CH | H | 2-Cl | 5-Cl | H | 224–225 |
| 13a | CH | H | 2-Cl | 4-Cl | 5-Cl | 280 |
| 14a | CH | H | 2-Cl | 4-Cl | H | 248–250 |
| 15a | CH | H | 2-Cl | 3-Cl | 4-Cl | 238 |
| 16a | CH | H | 3-Cl | 4-Cl | 5-Cl | |
| 17a | 2-N | H | 3-Cl | H | H | |
| 18a | CH | H | 3-Cl | 4-Cl | H | 188 |
| 19a | 3-N | H | 3-Cl | 4-Cl | H | |
| 20a | CH | H | 3-Cl | 5-Cl | H | 255 |
| 21a | CH | H | 3-Cl | H | H | 235 |
| 22a | CH | H | 4-Cl | H | H | 190–191 |
| 23a | CH | H | 3-Br | H | 5-F | |
| 24a | CH | H | 3-Br | 4-$OCF_2H$ | H | |
| 25a | CH | H | 3-Br | H | H | 227 |
| 26a | CH | $CO_2C_2H_5$ | 2-I | H | 5-F | |
| 27a | CH | H | 3-I | H | 5-I | |
| 28a | 3-N | $CH_3$ | 4-I | H | 5-Cl | |
| 29a | CH | H | 2-F | H | H | 220 |
| 30a | CH | H | 3-F | H | H | 205 |
| 31a | CH | H | 2-CN | 3-$CH_3$ | 4-$CF_3$ | |
| 32a | 3-N | H | 2-CN | H | H | |
| 33a | 3-N | $CH_3$ | 2-CN | H | H | |
| 34a | 2-N | H | 4-CN | H | H | |
| 35a | CH | H | 2-$NO_2$ | 4-Cl | H | |
| 36a | CH | $C_2H_5$ | 2-$NO_2$ | H | H | |
| 37a | CH | $(CH_2)_2CO_2CH_3$ | 2-$CH_3$ | 3-I | H | |
| 38a | CH | H | 2-$C_2H_5$ | 3-Cl | 5-Cl | |
| 39a | CH | $COCH_3$ | 2-i-$C_3H_7$ | 3-F | H | |
| 40a | CH | H | 2-$CF_3$ | H | H | 180–182 |
| 41a | CH | CHO | 2-$CF_3$ | 3-$OCH_3$ | H | |
| 42a | CH | $CH_3$ | 2-$OCF_2H$ | H | H | |
| 43a | 4-N | H | 3-$OCF_2H$ | H | H | |
| 44a | 4-N | H | 2-$OCH_3$ | H | H | |
| 45a | CH | H | 2-O-i-$C_3H_7$ | H | 5-Br | |
| 46a | CH | H | 2-$OCH_2CH=CH_2$ | 3-F | H | |
| 47a | CH | $CH_3$ | 2-$OCH_2C\equiv CH$ | 3-Cl | 4-Cl | |
| 48a | CH | H | 5-$OCH=CH_2$ | 4-Cl | 3-Cl | |
| 49a | CH | H | 2-O-$(CH_2)_2CO_2CH_3$ | H | 4-F | |
| 50a | CH | H | 5-$CONHC_2H_5$ | 3-Cl | H | |
| 51a | 4-N | $CH_3$ | 2-$CON(CH_3)_2$ | H | H | |

TABLE 2-continued

| Ex. No. | X | R¹ | R² | R³ | R⁴ | M.p. [° C.] |
|---|---|---|---|---|---|---|
| 52a | 3-N | H | 2-CONH₂ | H | H | |
| 53a | CH | COCH₃ | 3-CONH₂ | 5-Cl | H | |
| 54a | CH | (CH₂)₂OCH₃ | 3-COOH | 4-Br | 5-Cl | |
| 55a | 2-N | H | 4-COOH | H | H | |
| 56a | CH | H | 5-CO₂C₂H₅ | 3-Cl | H | |
| 57a | 2-N | H | 4-CONH-i-C₃H₇ | H | H | |
| 58a | CH | CO₂CH₃ | 4-SO₂CH₃ | 3-Cl | H | |
| 59a | CH | H | 2-Cl | 4-Cl | 6-Cl | 217–220 |
| 60a | CH | H | 2-Cl | H | 6-Cl | 211 |
| 61a | CH | H | 2-F | H | 5-F | 148–155 |
| 62a | CH | H | H | 4-CF₃ | H | 199 |
| 63a | CH | H | 2-CH₃ | 4-Cl | H | 222–226 |
| 64a | CH | H | 3-Cl | 4-CH₃ | H | 148–151 |
| 65a | CH | H | 2-F | 4-F | H | 187–192 |
| 66a | CH | H | 4-CH₃ | H | H | 226 |
| 67a | CH | H | 2-CH₃ | H | H | 210 |
| 68a | CH | H | 2-CH₃ | 5-CH₃ | H | 246 |
| 69a | CH | H | 2-CH₃ | 3-CH₃ | H | 132 |
| 70a | CH | H | 2-Cl | 5-CF₃ | H | 188 |
| 71a | CH | H | 3-OCH₃ | 5-OCH₃ | H | 187 |
| 72a | CH | H | 2-F | 3-Cl | 4-F | 193 |
| 73a | CH | H | 5-CONHC₂H₅ | 2-Cl | H | 294 |
| 74a | CH | H | 5-CONH-i-C₃H₇ | 2-Cl | H | 250 |
| 75a | CH | H | 5-CONH-t-C₄H₉ | 2-Cl | H | 170 |
| 76a | CH | H | 2-Cl | 3-CN | 4-Cl | 226–231 |
| 77a | CH | H | 2-F | 3-F | H | 156–161 |
| 78a | CH | H | 2-Br | 4-Br | H | 261 |
| 79a | CH | H | 2-Br | 3-F | H | 249 |
| 80 | 3-N | H | 4-Cl | H | H | |

In Tables 1 and 2, the position indicated for R¹, R², R³, R⁴ and, in the event of X equals N, also the position indicated for N, is to be understood as meaning such that the reference position 1 is attributed to the carbon atom in the benzene or pyridine ring on which linkage with the uracilylamino group takes place. The position of substituents R¹, R², R³, R⁴ and of N is then determined in accordance with the general numeration of known nomenclature rules.

The following comparison examples illustrate the possible uses of the compounds according to the invention.

In these examples, the abbreviations used denote:

Harmful Plants

| | | | |
|---|---|---|---|
| ABUTH | Abutilon theophrasti | PHBPU | Pharbitis purpurea |
| AGRRE | Elymus repens | POLPE | Polygonum sp. |
| ALOMY | Alopecurus myosuroides | SETVI | Setaria viridis |
| GALAP | Galium aparine | SORHA | Sorghum halepense |
| MATCH | Matricaria chamomilla | VERPE | Veronica persica |
| PANSS | Panicum sp. | | |

Crop Plant

| | |
|---|---|
| ZEAMX | Zea mays |

0=no damage
1=1–24% damage
2=25–74% damage
3=75–89% damage
4=90–100% damage

Use Example A

In the greenhouse, the plant species listed are treated post-emergence with the compound according to the invention at a rate of application of 0.03 kg of active ingredient/ha. To this end, the compound is sprayed uniformly over the plants in the form of an emulsion with 500 l of water/ha. After 2 weeks, it shows a very good activity against the harmful plants and better activity than the agent disclosed in WO 95/04461 and tested under the same conditions for the purpose of comparison.

| Test compounds | ALOMY | AGRRE | SETVI | PANSS | SORHA | ABUTH | GALAP | MATCH | POLPE | VERPE |
|---|---|---|---|---|---|---|---|---|---|---|
| 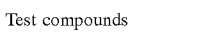 (Example No. 1) | 3 | 2 | 3 | 4 | 3 | 4 | 3 | 4 | 4 | 4 |

| Test compounds | ALOMY | AGRRE | SETVI | PANSS | SORHA | ABUTH | GALAP | MATCH | POLPE | VERPE |
|---|---|---|---|---|---|---|---|---|---|---|
| 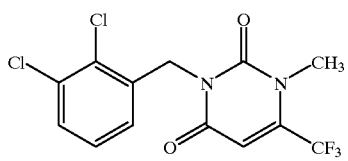 (WO 95/04461) | 2 | 1 | 2 | 3 | 2 | 4 | 3 | 3 | 4 | 3 |
| Untreated | 0 | 0 | 0 | 0 | 0 | 0 | 0 | 0 | 0 | 0 |

Use Example B

In the greenhouse, the plant species listed are treated pre-emergence with the compound according to the invention at a rate of application of 0.3 kg of active ingredient/ha. To this end, the compound is sprayed uniformly onto the soil which contains the seeds of the test plants in the form of an emulsion with 500 l of water/ha. 2 weeks after the treatment, it shows a very good activity against the harmful plants and a markedly better tolerance by maize than the agent disclosed in WO 95/04461 and tested under the same conditions for the purpose of comparison.

| Test compounds | ZEAMX | AGRRE | PHBPU | POLPE |
|---|---|---|---|---|
| (Example No. 2) | 0 | 4 | 4 | 4 |
| (WO 95/04461) | 3 | 4 | 4 | 4 |
| Untreated | 0 | 0 | 0 | 0 |

What is claimed is:

1. A substituted 3-arylamino-6-trifluoromethyluracil of the formula I

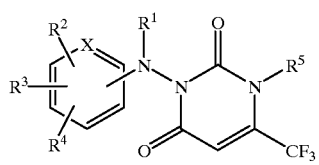

(I)

in which $R^1$ is hydrogen, $C_1$–$C_4$-alkyl, halo-$C_1$–$C_4$-alkyl, $C_1$–$C_4$-alkoxy-$C_1$–$C_4$-alkyl, $C_1$–$C_4$-alkoxycarbonyl-$C_1$–$C_4$-alkyl, formyl, $SO_2R^6$, $C_1$–$C_{10}$-alkylcarbonyl or $C_1$–$C_{10}$-alkoxycarbonyl, it being possible for the two last-mentioned radicals to be optionally substituted by one or more identical or different halogen atoms, $R^2$ is hydrogen, halogen, nitro, amino, cyano, $C_1$–$C_4$-alkyl, halo-$C_1$–$C_4$-alkyl, $C_1$–$C_4$-alkoxy, halo-$C_1$–$C_4$-alkoxy, $C_2$–$C_4$-alkenyloxy, $C_3$–$C_4$-alkynyloxy, $C_1$–$C_4$-alkoxycarbonyl, $C_1$–$C_4$-alkoxy-carbonyl-$C_1$–$C_4$-alkoxy, carboxyl, aminocarbonyl, $C_1$–$C_4$-alkylaminocarbonyl, di-$C_1$–$C_4$-alkylaminocarbonyl or $C_1$–$C_4$-alkyl-sulfonyl, $R^3$ and $R^4$ independently of each other are hydrogen, halogen, nitro, cyano, $C_1$–$C_4$-alkyl, halo-$C_1$–$C_4$-alkyl, $C_1$–$C_4$-alkoxy or halo-$C_1$–$C_4$-alkoxy, $R^5$ is $C_1$–$C_4$-alkyl or amino, $R^6$ is $C_1$–$C_6$-alkyl or $C_2$–$C_6$-alkenyl which is optionally substituted by one or more identical or different halogen atoms and X is CH or N.

2. A substituted 3-arylamino-6-trifluoromethyluracil of the formula I as claimed in claim 1, wherein $R^1$ is hydrogen, $C_1$–$C_3$-alkyl, $C_1$–$C_3$-alkyl which is mono- or polysubstituted by fluorine, chlorine or bromine, $C_1$–$C_4$-alkoxy-$C_1$–$C_2$-alkyl, $C_1$–$C_4$-alkoxycarbonyl-$C_1$–$C_2$-alkyl, formyl, $SO_2R^6$, $C_1$–$C_6$-alkylcarbonyl or $C_1$–$C_6$-alkoxycarbonyl, it being possible for the two last-mentioned radicals to be optionally substituted by one or more identical or different halogen atoms, $R^2$ is hydrogen, halogen, nitro, cyano, $C_1$–$C_3$-alkyl, $C_1$–$C_3$-alkyl which is mono- or polysubstituted by fluorine, chlorine or bromine, methoxy, ethoxy, propoxy, isopropoxy, $C_1$–$C_3$-alkoxy which is mono- or polysubstituted by fluorine, chlorine or bromine, $C_2$–$C_4$-alkenyloxy, $C_3$–$C_4$-alkynyloxy, $C_1$–$C_3$-alkoxy-carbonyl, $C_1$–$C_4$-alkoxycarbonyl-$C_1$–$C_2$-alkoxy, carboxyl, aminocarbonyl, $C_1$–$C_3$-alkylaminocarbonyl, di-$C_1$–$C_3$-alkylaminocarbonyl or $C_1$–$C_2$-alkylsulfonyl, $R^3$ and $R^4$ independently of one another are hydrogen, halogen, nitro, cyano, methyl, ethyl, trifluoromethyl, methoxy, ethoxy, propoxy, isopropoxy, $C_1$–$C_3$-alkoxy which is mono- or polysubstituted by fluorine, chlorine or bromine, $R^5$ is methyl, ethyl or amino, $R^6$ is $C_1$–$C_4$-alkyl or $C_2$–$C_4$-alkenyl which is optionally substituted by one or more identical or different halogen atoms, and X is CH or N.

3. A substituted 3-arylamino-6-trifluoromethyluracil of the formula I as claimed in claim 1, wherein $R^1$ is hydrogen, $C_1$–$C_3$-alkyl, $C_1$–$C_3$-alkyl which is mono- or polysubstituted by fluorine or chlorine, formyl, $SO_2R^6$, $C_1$–$C_4$-alkylcarbonyl or $C_1$–$C_4$-alkoxycarbonyl, the two last-mentioned radicals optionally being substituted by one or more identical or different halogen atoms, $R^2$ is hydrogen, halogen, nitro, amino, cyano, $C_1$–$C_2$-alkyl, $C_1$–$C_2$-alkyl which is mono- or polysubstituted by fluorine or chlorine, methoxy, ethoxy, propoxy, isopropoxy, $C_1$–$C_2$-alkoxy which is mono- or polysubstituted by fluorine or chlorine, $C_2$–$C_3$-alkenyloxy, $C_3$–$C_4$-alkynyloxy, $C_1$–$C_3$-alkoxycarbonyl, $C_1$–$C_2$-alkoxycarbonyl-$C_1$–$C_2$-alkoxy, carboxyl, aminocarbonyl, $C_1$–$C_2$-alkylaminocarbonyl, di-$C_1$–$C_2$-alkyl-aminocarbonyl or $C_1$–$C_2$-alkylsulfonyl, $R^3$ and $R^4$ independently of one another are hydrogen, halogen, methyl, ethyl, trifluoromethyl, methoxy, ethoxy, propoxy, isopropoxy, methoxy which is mono- or polysubstituted by fluorine or chlorine, $R^5$ is methyl, ethyl or amino, $R^6$ is $C_1$–$C_4$-alkyl or $C_2$–$C_4$-alkenyl which is optionally mono- or polysubstituted by identical or different halogen atoms from the group consisting of chlorine and fluorine, and X is CH or N.

4. A substituted 3-arylamino-6-trifluoromethyluracil of the formula II

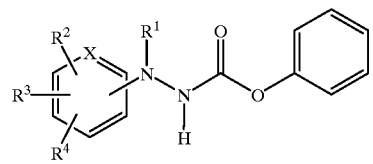

(II)

in which $R^1$, $R^2$, $R^3$, $R^4$ and X have the meanings given under formula I as intermediates for the preparation of a compound of the formula I as claimed in claim 1.

5. A process for the preparation of a compound of the formula I as claimed in claim 1, which comprises, in the event that $R^5$ in formula I is $C_1$–$C_4$-alkyl, A) reacting a compound of the formula II as claimed in claim 4 with an alkylating reagent or, in the event that $R^5$ in formula I is amino, B) reacting a compound of the formula II as claimed in claim 4, first of all, with a nitrosation reagent and then reacting the resulting N-nitrosamine with a complex hydride, or reacting a compound of the formula II as claimed in claim 4 with 2,4-dinitrophenoxyamine with base catalysis.

6. A process for the preparation of a compound of the formula II as claimed in claim 4, which comprises introducing ethyl 3-amino-4,4,4-trifluoromethyl-crotonate together with a base into an inert solvent and subsequently reacting it with a compound of the formula III

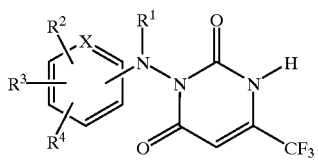

(III)

in which $R^1$, $R^2$, $R^3$, $R^4$ and X have the meanings given under formula I as set forth in claim 1.

7. A herbicidally active composition, which comprises at least one compound as claimed in claim 1.

8. A herbicidally active composition as claimed in claim 7 in the form of a mixture with carriers and/or surfactants.

9. A method of controlling monocotyledonous and dicotyledonous harmful plants in agricultural and silvicultural crops, which comprises applying at least one of the compounds as claimed in claim 1 to the location of the undesirable plant growth.

10. The method as claimed in claim 9, wherein the compounds are employed in the form of a mixture with carriers and/or surfactants.

* * * * *